(12) United States Patent
Hovig et al.

(10) Patent No.: US 6,607,886 B2
(45) Date of Patent: Aug. 19, 2003

(54) METHOD AND APPARATUS FOR SIMULTANEOUS QUANTIFICATION OF DIFFERENT RADIONUCLIDES IN A LARGE NUMBER OF REGIONS ON THE SURFACE OF A BIOLOGICAL MICROARRAY OR SIMILAR TEST OBJECTS

(75) Inventors: Eivind Hovig, Oslo (NO); Arne Skretting, Slependen (NO); Einar Nygard, Asker (NO); Yngve Kvinnsland, Rykkinn (NO); Knut Breistol, Oslo (NO); Koki Yoshioka, Oslo (NO)

(73) Assignee: Biomolex AS, Hovik (NO)

( * ) Notice: Subject to any disclaimer, the term of this patent is extended or adjusted under 35 U.S.C. 154(b) by 3 days.

(21) Appl. No.: 09/775,515

(22) Filed: Feb. 1, 2001

(65) Prior Publication Data

US 2002/0142301 A1 Oct. 3, 2002

(51) Int. Cl.$^7$ ............... C12Q 1/68; G01N 33/53; C12N 9/16; C12N 15/00; C07H 21/02

(52) U.S. Cl. ............... 435/6; 435/7.6; 435/320.1; 435/196; 536/23.1; 536/23.2; 536/24.1

(58) Field of Search ............... 435/6, 91.1, 320.1; 250/370.09; 536/23.1, 23.2, 24.1

(56) References Cited

U.S. PATENT DOCUMENTS

| | | | |
|---|---|---|---|
| 4,967,084 A | 10/1990 | Rich et al. | 250/361 R |
| 5,117,114 A | 5/1992 | Street et al. | 250/370.11 |
| 5,459,677 A | 10/1995 | Kowalski et al. | 364/571.02 |
| 5,656,818 A | 8/1997 | Nygård | 250/370.09 |
| 5,866,907 A | 2/1999 | Drukier et al. | 250/366 |
| 5,948,888 A * | 9/1999 | de la Monte et al. | |
| 6,297,013 B1 * | 10/2001 | Morgan et al. | |

FOREIGN PATENT DOCUMENTS

| | | |
|---|---|---|
| EP | 0 268 406 A2 | 5/1988 |
| EP | 0 853 427 A2 | 7/1998 |
| GB | 2 311 198 A | 9/1997 |
| WO | WO 98/53618 | 11/1998 |
| WO | WO 99/08233 | 2/1999 |

OTHER PUBLICATIONS

Kvinnsland, K., Methods for separation of contribution from two radionuclides in autoradiography. . . , Phys. Med. Biol. 45, 2000 pp. 1183–1193.*

Wang E. et al., "Highly–fidelity mRNA amplification for gene profiling", *Nat Biotechnology* 2000 18(4) :457–459.

Nilsen T.W. et al., "Dendritic Nucleic Acid Structures", *J. Theor. Biol.* 1997 187:273–284.

Wang J. et al., "Adsorption and Detection of DNA Dendrimers at Carbon Electrodes", *Electroanalysis* 1998 10 (8) :553–556.

Wang J. et al., Dendritic Nucleic Acid Probes for DNA Biosensors, *J. Am. Chem. Soc.* 1998 120:8281–8282.

Kvinnsland Y. et al., "Methods for separation of contributions from two radionuclides in autoradiography with a silicon strip detector", *Phys. Med. Biol.* 2000 45:1183–1193.

* cited by examiner

Primary Examiner—W. Gary Jones
Assistant Examiner—Arun Kr. Chakrabarti
(74) Attorney, Agent, or Firm—Licata & Tyrrell P.C.

(57) ABSTRACT

The present invention relates to a method and apparatus for simultaneous quantification of the amounts of one or more radioactive nuclides within arbitrary regions on a surface where these nuclides have been deposited, adsorbed or fixed. These radioactive nuclides serve as markers on compounds that typically have been incorporated into tissue sections or into larger biological molecules that by various mechanisms have been bound to chemical substances on this surface. The method is especially well suited for DNA microarray deductions through the use of nucleotides labelled with different beta-emitting radionuclides.

12 Claims, 5 Drawing Sheets

METHOD AND APPARATUS FOR SIMULTANEOUS QUANTIFICATION OF DIFFERENT RADIONUCLIDES IN A LARGE NUMBER OF REGIONS ON THE SURFACE OF A BIOLOGICAL MICROARRAY OR SIMILAR TEST OBJECTS

TECHNICAL FIELD

The present invention relates to a method and apparatus for simultaneous quantification of the amounts of one or more radioactive nuclides within arbitrary regions on a surface where these nuclides have been deposited, adsorbed or fixed. These radioactive nuclides serve as markers on compounds that typically have been incorporated into tissue sections or into larger biological molecules that by various mechanisms have been bound to chemical substances on this surface. The method is especially well suited for DNA microarray deductions through the use of nucleotides labelled with different beta-emitting radionuclides.

BACKGROUND

It is widely believed that thousands of genes and their products, i.e. RNA and proteins, in a living organism function in a complicated and orchestrated way that creates the mystery of life. However, traditional methods in molecular biology generally work on a "one gene in one experiment" basis, which makes it hard to achieve the overall picture of the gene function. Thus, biological microarrays represents one of the most potent new tools in biological research to emerge in recent years, since it gives the opportunity to study a complete set of genes and their products simultaneously.

A microarray is an ordered arrangement of biological molecules immobilised in sample spots on a test plate which provides a medium for matching known and unknown samples of biological molecules. The immobilised molecules on the test plate are often denoted probe molecules, while the biological molecules from the test samples are denoted target molecules. In the case when the probe molecules and target molecules forms specific complementary pairs of biological molecules, the ordered arrangement of the test spots can be employed to identify specific biological molecules in a test sample from an organism and also to determine the abundance of these molecules. Typical examples of complementary biological molecules are hybridisation pairs of DNA, gene-anti gene etc. In microarrays the sample spots are typically less than 200 $\mu$m in diameter, but there "macroarrays" with sample spots with diameters of typically 300 $\mu$m or larger have been described.

The biological microarray technique can be applied for numerous applications such as diagnosis, identification/discovery of new genes and proteins, drug discovery, pharmacological and toxicological research etc. The technique can also be employed to comparison tests where biological components from several sources are adsorbed onto the same array, for instance from a healthy cell and a tumour cell.

Among biological microarrays, it is especially one type that has drawn attention the latest years; the DNA-microarray. This technology promises to monitor the whole genome on a single chip, and thereby make it possible to acquire a better picture of the interactions between thousands of genes simultaneously.

PRIOR ART

In general, the conventional method of determining biological activity by DNA-microarrays can be described as follows; strands of probe cDNA (typically 500–5000 bases long) are immobilised in a specific and ordered array onto a solid plate (typically a glass plate). Then the probe cDNA is exposed to one or several targets (marked cDNA from the test samples) either separately or in a mixture. The targets, labelled cDNA, are produced enzymatically by reverse transcriptase from samples of RNA which are extracted from the test samples and labelled with specific marker molecules. The reverse-transcribed RNA transcripts of the samples are hybridised with the probe cDNA on the microarray. Thus the amount and type of each target cDNA can be determined by measuring the location and concentration of each marker molecule at each test spot on the microarray, since the marker signal from each test spot reflects the relative transcript amounts for each specific transcript at each test spot on the microarray. To eliminate sample variation, the signal ratio between two competing samples is the preferred measurement.

Fluorescence Tagged Nucleotides

Traditionally, the detection of signals using this technology has been based on in vitro incorporated nucleotides labelled with suitable fluorophores, that is, specific fluorophores (fluorescence molecules) of a distinctive colour are inserted into the RNA extracted from each sample, respectively. Thus nucleotides labelled with fluorophores of a distinctive colour are incorporated into the target cDNA which will be hybridised to the probe cDNA. The fluorophores may be excited by different wavelengths, and similarly also emit at different wavelengths. Laser light and the use of appropriate filters to separate signals from two or more cDNA populations will generally achieve this.

However, the general need for starting material is in the range of 50 $\mu$g of total RNA, or approximately 5×10$^7$ cell equivalents. This relatively high amount of material excludes the use of standard technology from a number of very relevant applications, including clinical diagnostics. One highly significant factor in this lack of sensitivity is the low incorporation rate of current fluorophore-tagged nucleotides in the reverse transcription of cDNA from RNA. Thus only a relatively low number of fluorescence molecules will be incorporated per synthesised cDNA. Also, applications requiring incorporation of fluorescence through cell culture will be excluded, as fluorophore-tagged nucleotides will generally not be included through the cellular machinery. Emerging techniques to achieve better signal strength include enzymatic amplification of sample material and chemical signal amplification. Such methods demonstrate that it is possible to reduce sample size.

Amplification techniques have recently been published allowing a reduction in sample size down to 100 ng total RNA starting material (Wang, E. et al. *Marincola FM Nat Biotechnol* 2000.18(4):457–459). This is achieved through one or more rounds of cycling between RNA and cDNA. In this reaction it is possible in each round to obtain approximately a 50-fold increase of the material by attaching a T7 promoter at one end to enable generation of RNA, and at the other end exploiting a feature of certain reverse transcriptases to add a specific primer to all cDNAs at most 5' end at the time of first reverse transcription. This feature is necessary to avoid generation of shorter length cDNAs.

An alternative strategy is to amplify the signal from the test material through chemical means. The most sensitive strategy so far available relies on nested tangles of labelled branched synthetic DNA molecules (Nilsen, T. W. et al. *J. Theor. Biol.* 1997.187:273–284; Wang, J. et al. *Electroanalysis* 1998.10:553–556; Wang, J. et al. *J. Am. Chem. Soc.* 1998.120:8281–8282). These may be bound to poly-A tails of cDNA prior to array hybridisation. Generally, a 250-fold increase in signal strength may be achieved.

Neither of these strategies have been rigorously tested for reliable performance and sensitivity levels. It is likely that amplification techniques will lead to degrees of bias of the starting material, due to the enzymatic nature of the process combined with the large variation in mRNA length for different transcripts.

The large amount of test material necessary to achieve adequate signal strength, and the problem that the available fluorophores are accepted only with difficulty by the reverse transcriptase enzyme represents thus considerable disadvantages in the prior art.

Radioactivity Labelled Nucleotides

It is known that the problem with low acceptance by the reverse transcriptase enzyme can be solved by employing radioactive isotopes for the labelling of nucleotides.

Historically, radioactive isotopes have been in widespread use for sensitive detection and quantification of nucleic acids. The common use has been confined to the use of one single, usually beta-emitting, radionuclide, incorporated either into a probe (detector nucleic acid) or directly in vivo. The detection has been performed using liquid scintillation or gamma counters, and in the case of a two-dimensional distribution (e.g. Northern and Southern blots), autoradiography film, phosphor imagers, and digital autoradiography systems has been employed (ref. French patent BioSpace, Cern patent, Charpak).

Measurements of the distribution of a radioactive compound in a thin section of tissue or Southern and Northern nucleic acid blots has traditionally been performed with film autoradiography, and this method still remains the common choice for fine resolution studies. However, it suffers from a limited dynamic range (only 1.5–3 orders of magnitude) and low sensitivity, is laborious and gives inaccurate determinations.

Storage phosphor screen imaging systems have a much better sensitivity than film autoradiography, 250 times more sensitive than X-ray film with $^{32}P$ and 60–100 times more sensitive than direct film autoradiography with $^{14}C$ and $^{35}S$. The linear dynamic range of these systems are 4–5 orders of magnitude and quantification methods give results that are much more reliable than with film. However, areas having activities below the minimum threshold are not quantified accurately, and inevitably imposes a limitation to the accuracy in measurements of activity distributions. A major practical problem of the two latter radiography modalities is the need to know the exposure time before acquiring the picture so that underexposure or overexposure may be avoided. Especially with film, where exposure times may be months, a bad estimate of the exposure time may cause waste of a considerable time.

The problems associated with the two latter radiography modalities can largely be solved by employing digital systems with direct event detection. This give results with absolute linearity, the count rate is only limited by the speed of the electronics, and the need for accurate estimates of exposure times is eliminated as one can inspect the cumulative pictures at any time. Even though the geometrical resolution of the available systems cannot compete with that of the film technique, it is comparable with phosphor screen imaging systems.

However, these techniques can not separate the contributions from different non-monoenergetic nuclides, and thus cannot be applied for simultaneous quantification of two or more different radioactive emitters at the same spot on a biological microarray. Obviously, this impedes (hinders) every application where one wants to simultaneously compare the activity from more than one specimen, such as for instance a healthy cell and a tumour cell. Thus a whole class of important diagnostic and research applications is cut off from the benefits of tagging nucleotides and/or other biological molecules with radioactive isotopes.

Also, according to our knowledge, the known methods and apparatuses for performing the conventional radiography methods are all limited to labelling all molecules on the surface with only one radio nuclide at time and a limited number of radio isotopes. Thus there is a need for a general method for performing simultaneous determinations of the radioactivity/intensity of two or more different radio nuclides at each spot in a biological microarray. A gamma camera equipped with a parallel hole collimator may be used to simultaneously measure the distribution of several gamma-emitting radio nuclides on a surface. However, this camera cannot resolve structures with spatial extent on the sub millimeter scale.

OBJECTIVE OF THE INVENTION

The main objective of this invention is to provide a method and apparatus for performing simultaneous quantifications and/or comparisons of one or more target biological molecules that are distinctively marked with radioactive isotopes and then adsorbed onto a probe array of biological molecules deposited on a substrate, and which substantially eliminates or reduces the above mentioned problems.

An additional objective of this invention is to provide a specific method and apparatus for simultaneous determination of two or more cDNAs which are labelled with beta emitting radionuclides with distinctive distributions, and which then are adsorbed onto a DNA-microarray.

BRIEF DESCRIPTION OF THE INVENTION

The above mentioned objectives can be obtained by the features as set forth in the following description and accompanying claims.

The objects of this invention can be obtained by exploiting a digital detection system capable of a) recording the position and energy of each particle/photon that hits a detector surface, b) performing a real-time rearrangement and data reduction, and c) simultaneously estimating from the rearranged data the quantities of two or more radio nuclides present within an arbitrary region of a probe surface, e.g. by the methods recently published by Kvinnsland and Skretting (Kvinnsland, Y. et al. *Phys. Med. Biol.* 2000.45:1183–1193) for separating the contributions from two radioactive nuclides in an autoradiography picture.

The digital detection system or apparatus includes an electronic device for detection and imaging of small radioactive samples which is capable of registering and recording the deposited energy and position of each radioactive particle that penetrates the instrument's sensor system. This device is a further development of the instrument disclosed in U.S. Pat. No. 5,656,818 and EP 0 983 705, thus, both patents are enclosed by reference. The working principle of the instrument is substantially the same as the instrument disclosed in the above cited patents. Thus we will only give a summary of the working principle of the instrument here, which may be considered as consisting of two main parts:

1. A monolithic semiconductor sensor designed as a single plate. The plate should preferably have a larger, or at least an equal surface area than the biological microarray. Typical dimensions will be an area in the order of ten square-centimeters and a thickness of about 300 $\mu$m. The surface of the monolithic semiconductor plate is covered on one side with parallel bands or "strips" of a sensitive p-type material, and the other side is covered with parallel bands or strips of a n-type material. The n-type bands are perpendicular to the p-type bands. Thus on each intersection of the bands, a pn-diode is formed, and the bands will thus form a matrix that provides a two-dimensional reading of the hit position of the radioactive particle. That is, as long as the pn-diodes are reverse biased, they will respond with a current pulse at the two orthogonal strips they are connected to when a radioactive particle penetrates the bulk of the diode. The strip pitch is typically in the order of 50 $\mu$m. Thus for a sensitive area of 64 mm×32 mm, there will be 1280×640 strips, giving the instrument a two-dimensional grid of 820 000 pixels. The semiconductor sensor plate can be made to respond to all types of radioactive particles, including $\alpha$, $\beta$, $\gamma$, and positron radiation. Depending on the energy levels and type of radioactivity, monolithic plates of Si, GaAs, CdTe, or CdZnTe etc. can be employed.

2. An electronic system for reading out the signals from the sensor. The system consist of Multi-Chip-Modules (MCM's) surrounding the sensor plate, and which comprises several parallel FE-chips (ASIC) each with an array of preamplifier and noise-filtering amplification channels. For each radioactive particle that impinges the sensor, the charge from the sensor x- and y-strip with the largest signal plus the two neighbouring strips, will have their charge-signal integrated and filtered by the corresponding channels in the corresponding FE-chips. The amplified signal of the x- and the y-side is read out from the MCM's by a Data-Acquisition-System (DAQ) and the controlling computer thus receives the x-y coordinate of the impinging radioactive particle together with the energy of the event.

By employing this specific combination of solid state technology and highly integrated read-out electronics, one achieves a highly sensitive accurate and reliable instrument which records the position and energy of each radioactive particle that penetrates the sensor plate of the instrument. Thus by placing the sensor plate in close contact with the biological microarray, one can measure the radioactivity from each test spot on the biological microarray. In order to make the instrument versatile and suitable for different types of radiation, it is envisioned that the instrument is equipped with replaceable sensor plates which have equal dimension but are made of different monolithic semiconductor materials, and which can easily be inserted into the integrated read-out electronics. Thus as an example, if one employs a sensor plate made of silicon which responds well to $\beta$-radiation, and then wants to investigate a biological microarray tagged with $\gamma$-emitters, the instrument can momentarily be made ready for this by substituting the silicon sensor plate with a sensor plate made of cadmium-zinc-tellurium which responds well to $\gamma$-radiation.

During registration, the microarray glass-plate is placed face down in close contact with the semiconductor sensor plate of the instrument, separated by a 1, 3 $\mu$m thick mylar foil. Thus the detector system will, due to its two-dimensional pattern of pn-diodes, register both the energy of the incoming radioactive particle and the position on the biological microarray it originated from. This implies that the summed emission-intensity must be sufficiently low to allow the instrument to register one by one emission event. The maximal activity that can be reliably measured is in the entire surface ranges from cosmic background radiation (approx. 1 Bq) up to 10 MBq, but for many practical applications a limitation of 4–6 kBq is preferred.

However in the case of $\beta$-emitters, there is a general problem with comparisons and/or simultaneous determinations of the activity since they emit at several energy levels, usually forming continuous energy spectra. That is, even if one employs two radioactive isotopes that emits $\beta$-particles with mean energies that are well distinctive, one cannot determine directly by the aid of the registered particle energy from which of the two isotopes the registered particle originated from. However, the energy spectra of the two isotopes can be measured for each radio nuclide separately, and these spectra can be employed to separate the contributions from each isotope as long as the isotopes have spectra that are sufficiently different.

In the method according to this invention, the energy spectra of the isotopes are formed by dividing the total energy span of the emitted $\beta$-particles into a vector of k discrete energy bins, where k is a positive integer which preferably should be larger than 20. That is, for each region, r, on the probe surface, the registered $\beta$-particles are classified according to which of the k'th energy bin they belong to. Thus a discrete vector representation of the actual energy spectrum, $$E_{rk} = \sum_{ij \in r} E_{ijk},$$

of the isotopes for each region on the probe surface is achieved. As a result of the real-time data rearrangement and possible subsequent reduction the instrument provides at the end of a pre-set measuring period, image information in the form of an image containing k energy bands (energy band images), in analogy to a colour image that contain these bands as a red, blue, green colour etc. One element of an energy band image, denoted $E_{i,j,k}$, contains the number of particles within the k'th energy interval that were recorded at digital coordinate i,j.

For any image region, r, the registered discrete energy histogram $E_{rk}$ is a linear combination of the known energy spectra from each of the actual radioactive isotopes. In the following we will illustrate the method in the case when two isotopes are applied, but one should have in mind that the method can be applied for any number of isotopes. If the known energy spectra were acquired with identical energy bins as was used for acquisition of the energy band image, and normalised so that the sum over all bins equals 1, the calculations can be performed as follows:

Let $s_{Ak}$ and $s_{Bk}$ denote the energy spectra at bin k obtained with pure samples of isotope A and B respectively. Further, let $a_r$ and $b_r$ be the unknown contributions within region r (total number of recorded emissions) from isotope A and B, respectively. It is important that the energy bins of the reference spectra are identical to those used during the data acquisition of the actual measurement leading to the energy band images ($E_{rk}$).

Then:

$$E_{rk} = s_{Ak} a_r + s_{Bk} b_r \qquad (1)$$

These relationships can be employed in one of the above mentioned algorithms from the article by (Kvinnsland and Skretting, 2000) to estimate contribution $a_r$ and $b_r$ for each region on the probe surface. The article gives two general algorithms, the least square method (LS) and maximum likelihood method (ML). Both are incorporated here as a reference, and all we need to say is that the LS-algorithm is the simplest and requires considerable less computing power than the ML-algorithm, but suffers from a slightly larger inaccuracy in the estimates. Thus we will focus on the LS-algorithm in the following discussion, but nevertheless emphasise that both algorithms are incorporated in the invention.

In principle the LS-algorithm works as follows: The aim is to find which contributions $a_r$ and $b_r$ gives the least error sum S over the whole vector, where S is given as:

$$S = \sum_{i=1}^{k} (E_i - s_{Ai} a_i - s_{Bi} b_i)^2 \qquad (2)$$

The minima is determined by:

$$\frac{\partial S}{\partial a} = 0 \text{ and } \frac{\partial S}{\partial b} = 0 \qquad (3)$$

As mentioned, the method is given as a determination of the contribution from two isotopes. The method can however be employed for any number of isotopes by simply adding a term of type "s*c" for each additional isotope in the equations. In practice, the method is employed as follows: For each pixel ij of the sensor plate, there a vector $E_{ijk}$ with k counters is established in the memory system of the instrument. The entire data set, $E_{ijk}$, is initially set equal to zero. When the x'th, y'th pixel registers a β-particle, the x'th, y'th counter with appropriate bin number k is increased by one. This process continues until a sufficient number of events are registered to give a statistical representation of the energy spectrum which then is applied in the one of the algorithms to determine the contribution from isotope A and B in the registered energy histogram at each region r of the probe surface.

In order to obtain a flexible instrument for a wide range of applications, the instrument is equipped with a very high resolution sensor plate containing a large number of pixels. Thus, for many applications the resolution of the biological microarray will be coarser than the resolution of the sensor plate. In these cases, considerable computing time can be saved if the registered data from neighbouring pixels can be condensed by adding them to the centre pixel. That is, by adding e.g. the registered events in one pixel and all of its nearest surrounding neighbours (a total of 9 pixels) into the centre pixel, the resolution and thus number of computations are decreased by a factor 9. If even coarser resolution is wanted one can include all neighbour pixels in two surrounding rows (a total of 25 pixels) and so forth. In this way we simulate a coarser sensor resolution and thus reduces the necessary computing steps accordingly. The spatial condensing into regions does also give an important increase in number of registered events for each element $E_{rk}$, in the resulting condensed energy band image, thus leading to an improved statistical accuracy of the estimated contributions.

Also, the method requires advance knowledge of the expected energy spectrum of each actual radionuclide. This can be obtained by calibration of the instrument with surface distributed sources of each of the actual radionuclides before determination of the unknown sample. The calibration procedure is incorporated as an automatic procedure in the instrument, where measured spectra are obtained for each of one side (the x-side) strips of the sensor plate. By determining the first and second moment of these spectra, their zero offset and gain with reference to a reference strip can be determined (note that for the calibration procedure, neighbour strip deposited energies are not taken into account). These calibration data can then be used in real time to correct the energy of each detected radioactive event. Also, this calibration procedure avoids problems encountered with external photon (gamma) sources where scattered radiation gives rise to changes of the spectra.

Since the glass plate containing the biological microarray may be slightly rotated with respect to the principal axes of the instrument, the rotation angle must be determined so that the test spots on the microarray form exactly vertical and horizontal rows and columns in the image. The determination of the optimal angle may be carried out as follows: A sum image is formed by adding all bands in the energy band images, $E_{ijk}$, i.e. summation over the index k. This image is then rotated in steps of 0.1 degrees, and for each new angle, the projection of the image on the x- and y-axes, respectively, are calculated. The optimal rotation angle corresponds to the maximum of the variance (i.e. the maximal contrast variation). The projections can easily be used to determine the upper, lower, leftmost, and rightmost position of a test spot. Thus, identification of a test spot is easy, and the associated region occupied by that test spot can be identified. It is thus possible to create a new energy band image where each point corresponds to the region occupied by one test spot. This will significantly strengthen the statistical accuracy of the final results.

This method and apparatus have been described as a general approach suitable for simultaneous determinations of the contribution from more than one radioactive isotope of a registered energy spectrum, which is a superimposition of unknown quantities from each isotope. The method is obviously necessary in the case of β-emitters since these have overlapping energies, but may seem unnecessary for other types of radiation (α, γ) which has a monoenergetic nature and thus gives very distinct energy spectra which in general do not overlap each other. But the method according to this invention may be beneficial even for these cases since the method allows to employ radioactive isotopes which emit photons or particles with small energy differences because the method will separate possible overlapping energy contributions. Also, the method will automatically treat the problem with secondary registrations due to background radiation and unavoidable scattering, and thus give determinations with excellent precision. This feature is an obvious benefit for all types of radiation.

DETAILED DESCRIPTION OF THE INVENTION

The invention will now be described in detail with reference to the enclosed drawings and an example of a preferred embodiment of the invention.

Figures 1A, 1B:
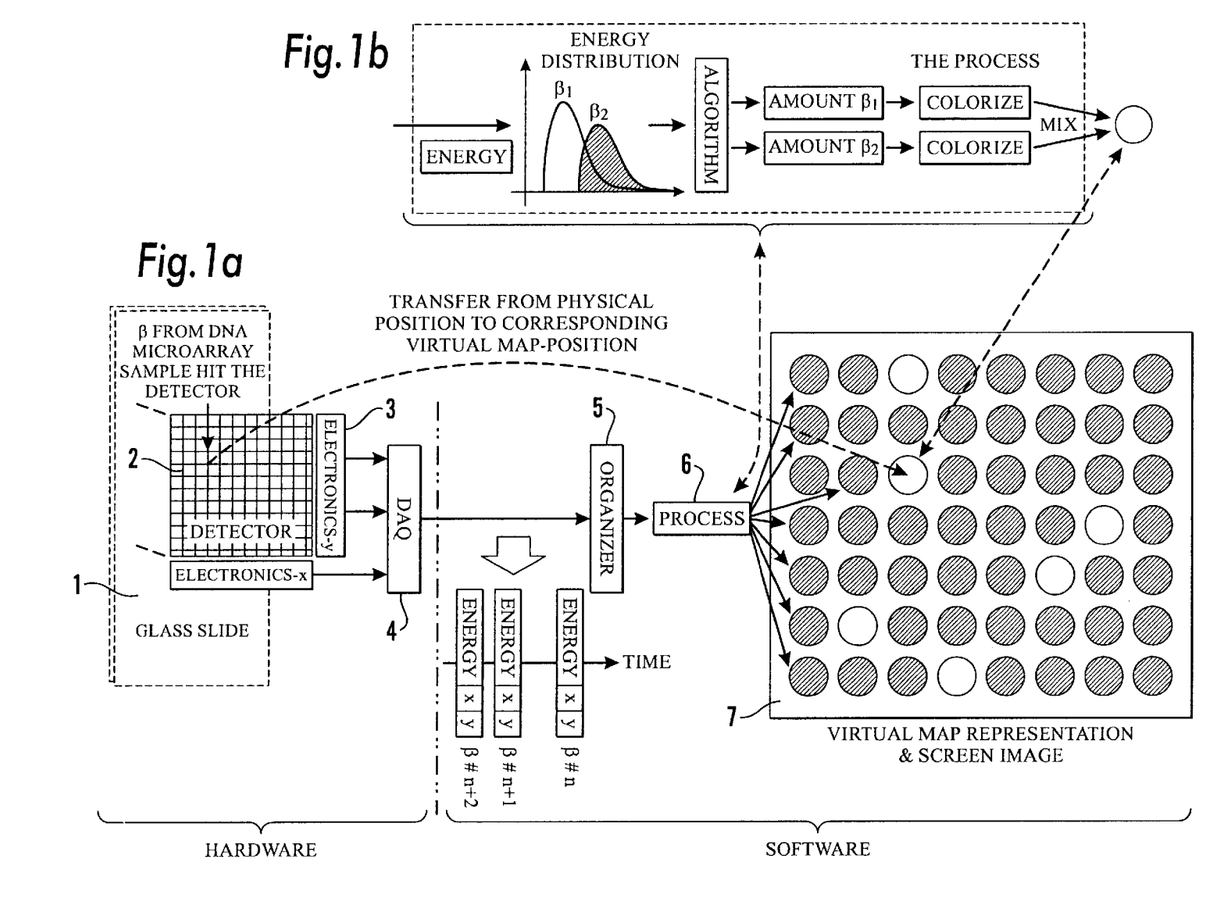
FIG. 1 is a flowchart schematically illustrating a preferred embodiment of the invention in the case of simultaneous determination of two or more cDNAs which are labelled with beta emitting radionuclides with distinctive distributions, and which then are adsorbed onto a DNA-microarray.
Figure 2:
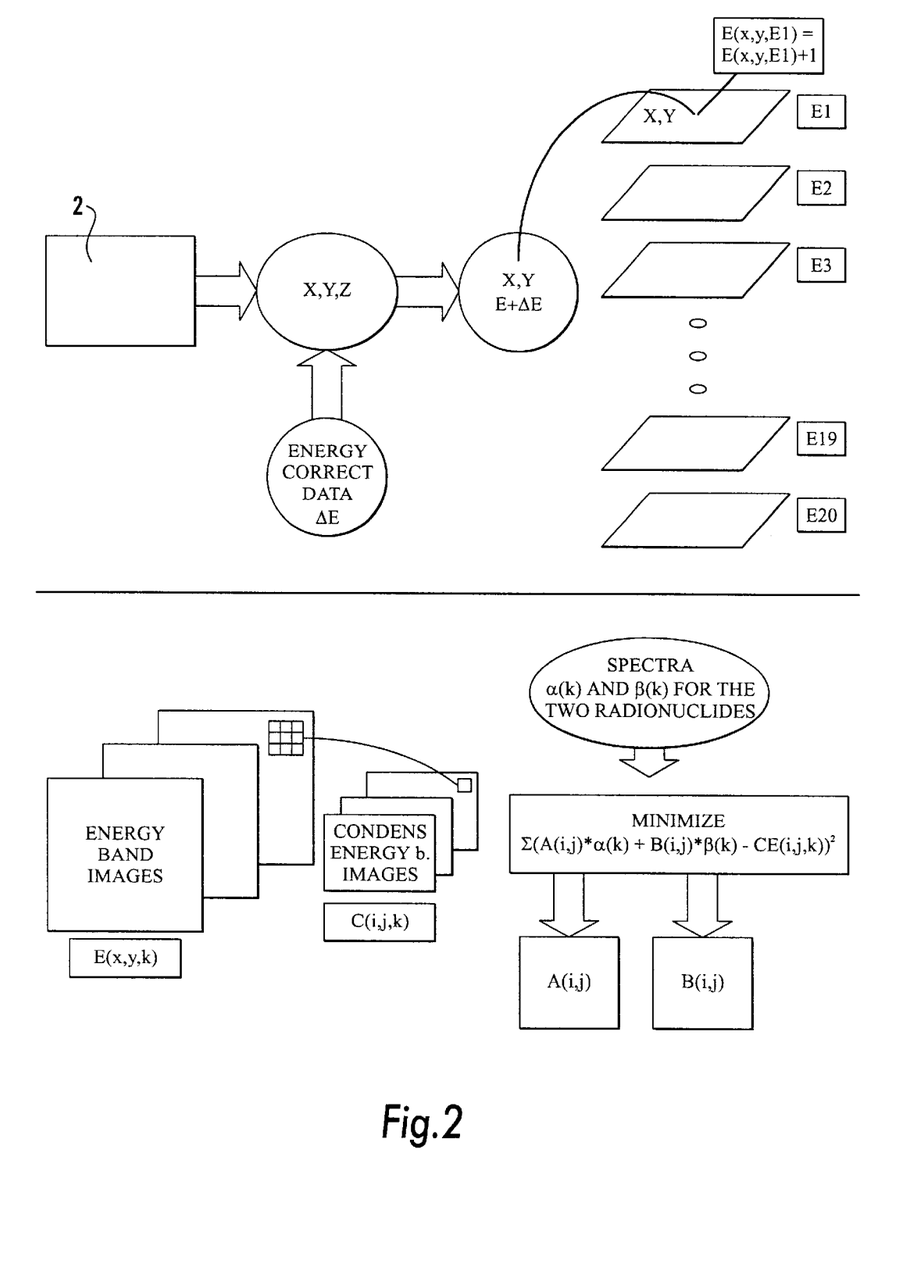
FIG. 2 is a block diagram schematically illustrating the data processing for separating the contribution from each radio isotope.
Figure 3:
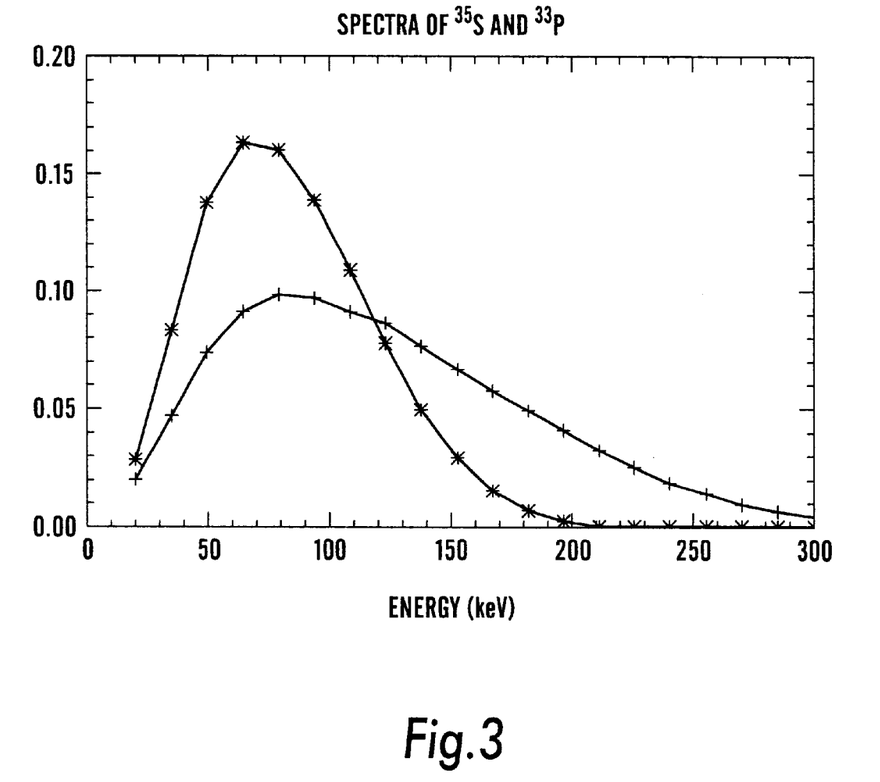
FIG. 3 is a chart showing the energy spectra for $^{33}P$ and $^{35}S$ isotopes as measured by the apparatus according to the invention, using the actual numbers of energy intervals (energy bins).

FIGS. 1 and 2 give a schematic representation of a preferred embodiment of the method and apparatus according to invention. The example is given in the case of determining the activity of DNA-molecules that are marked with two distinctive β-emitters and adsorbed onto a DNA-microarray. From the discussion above, the energy spectrum of the two radionuclides should be essentially distinct and have appropriate decay properties and energy levels, making the beta emission detectable within a suitable time range. Two suitable radionuclides for this purpose are $^{35}$P and $^{33}$S. The energy spectra of pure samples of these isotopes are given in FIG. 3.

In FIG. 1, a glass slide containing a DNA-microarray labelled with unknown quantities of the radioactive β-emitters $^{35}$P and $^{33}$S are marked with numeral 1. The glass slide is placed beneath and pressed towards a quadratic monolithic semiconductor sensor plate 2 made of silicon in such a manner that the DNA-microarray is covered by the sensor plate. The sensor plate 2 and the DNA-microarray are separated by a 1, 3 µm thick mylar foil (not shown). Thus, when a β-particle is emitted from one of the radionuclides, it will hit the sensor plate 2 and create a small current pulse in a pn-diode which lies substantially directly above the radionuclide that emitted the β-particle. Due to the two-dimensional network of such pn-diodes (also called pixels) in the sensor plate 2, the electronic system 3 of the apparatus will pick up the position (x,y-coordinate) of the pixel and thus the actual test spot on the DNA-microarray from which the β-particle originated. The electronic system will also measure the energy of the β-particle and send this information in digital form to a data acquisition unit 4 which accumulates all recorded events and organises them according to the registered position and energy. The data acquisition unit 4 may comprise any conventional digital storage unit such as RAM-memory chips, hard-disc, floppy-disc, CD-ROM etc. When the data acquisition unit has received sufficient data for making a statistically reliable analysis, i.e. when the elements of $E_{ijk}$ carry sufficient information the registration of events from the sensor plate is stopped. Then the recorded energy band image constitutes the input for the software program that determines the amounts of each isotope for every pixel, or after a condensation into regions as described earlier, at every test spot on the microarray by employing one of the algorithms given in Kvinnsland and Skretting [5]. That is, the algorithm determines how much (with how many registered events) each radionuclide did contribute to $E_{ijk}$, or $E_{rk}$ in the case of a larger spot (A proper quantification will of course require knowledge of the nucleotides half-time and the detector sensitivity for the actual radionuclide (registered events per unit of activity on the surface)). This procedure is schematically given in the highlighted box in FIG. 1 and in FIG. 2. The figures depict a case with two β-emitting radionuclides that are being determined by the least-square algorithm and where the pixels are condensed by a factor of 9 (all surrounding pixels in one layer are added into the centre pixel).

One advantage with this method is that the amounts of each isotope at every test spot are determined in absolute quantities. This gives several options for presenting the information. One option in the case of two isotopes is to determine the ratio of the isotopes at each spot and present this in a virtual map representing the biological microarray. Another option can mimic in a single image the colours obtained with red/green fluorophore techniques: By assigning the intensity of the image of one of the radionuclides in a red colour and the other in a green colour, a colour scale that mixes red and green in different proportions is created. It is also possible to present histogram-charts which show the absolute quantities of each radionuclide.

Determination of Absolute Quantities of RNA

The feasibility of the preferred embodiment of the method and apparatus will now be demonstrated in the case of determinations of absolute quantities of RNA marked with known quantities of $^{35}$P and $^{33}$S.

After calibration of the instrument, and prior to the measurements of the DNA microarray, the spectra of $^{33}$P and $^{35}$S were measured separately as follows: Solutions of the radionuclides were deposited evenly on glass slides and allowed to dry. The multiple energy band images obtained with these slides had an energy bin size of 15 keV, and there were 20 bins starting at a lower threshold of 20 keV. The spectra were spectra were created using the same bin sizes and number of bins and assumed to be independent of the position on the detector, therefore the entire images contributed to the spectra. For each pixel (or dot), the unknown contributions P and S from $^{33}$P and $^{35}$S respectively, were determined by the regression analysis and also by the Maximum Likelihood procedure. The resulting images P and S were displayed as one single image in the mode commonly used for presentation of images obtained with fluorophores. The phosphorus image (P) was sent to the red channel of the display, and the sulphur image was sent to the green channel. Equal amounts of red and green thus gave a yellow colour.

The DNA-arrays of all examples were produced adhering to the following protocol:

Coating:

Poly-L-lysine coated pre-cleaned microscope slides from J. Melvin Freed Brand (Sigma.Cat.No.S-8902) with dimension 75×25 mm were employed for printing. The slides were lysine-coated by placing them in a NaOH/EtOH-solution for 2 hours on an orbital shaker (75 g NaOH, 300 ml ddH$_2$O, and 450 ml 96% EtOH), then transferred to high purity water (double distilled, ddH$_2$O) and plunged up and down at least 10 times until the slide surface became clear. The slides were then repeatedly rinsed in fresh ddH$_2$O with shaking, soaked in poly-L-lysine solution (40 ml poly-L-lys:Lne, 40 ml PBS and 300 ml ddH$_2$O) on an orbital shaker for 1 hour. Finally, the slides were repeatedly rinsed in ddH$_2$C and then spun dry (500 rcf for 5 minutes) followed by exposure to 55° C. for 1 hour. The slides were allowed to age for at least two weeks at room temperature before printing.

Printing:

A home made robot was employed as an array printer, made by a description from P. Meltzer at NIH. Carbide split pins produced by Beecher Inc. were used, printing 48 slides with 8 pins (2×4) in one run. The pins were rinsed by soaking them in 1M NaOH for 2 minutes, followed by 10% SDS for 2 minutes and a short wash in ddH$_2$O. Then they were given a short ultrasonic treatment for 10 seconds before an additional rinsing in ddH$_2$O. The pins were then blown dry with pressurized air. The DNA was printed directly from Costar 96-wells plates (U-bottom, polystyrene cat.no.3367), where DNA PCR products were precipitated and dissolved in 25 µl 3×SSC. The printing were performed with a humidity of about 50%. The temperature was about 27–30° C. during the printing session. It were employed arrays containing 2200–2700 genes.

Post-processing:

The slides were treated with a UV-dose of 100 mJ to cross-link DNA to poly-L-lysine. A blocking solution was made by dissolving 6.0 g of succinic anhydride in 335 ml 1-methyl-2-pyrrolidinone and 15 ml of 1 M Boric acid (pH 8.0) under stirring. The slides were then submerged and plunged into the solution and put on an orbital shaker for 15–20 minutes. The slides were given a short rinse in $ddH_2O$, then submerged in hot water (95° C.) for 2 minutes and then transferred to cold 96% EtOH for 30 seconds. Finally the slides were dried (500 rcf. for 5 minutes) and stored, ready for use.

The preparation of radioactive cDNA probes for all experiments were performed according to the following protocol:

Conversion of 2–5 µg of Total RNA into $^{33}P/^{35}S$-labelled First Strand cDNA:

An a-33P-dATP, 10 mCi/ml, cat. no. AH9904, Amersham Pharmacia Biotech and an a-35S-dATP, 10 mCi/ml, cat. no. AG1000, Amersham Pharmacia Biotech were used for incorporation of radioactivity.

RT-reaction was made on ice:

| | |
|---|---|
| 5 x First strand reaction buffer | 4.0 µl |
| RNasin | 0.5 µl |
| DTT 100 mM | 2.0 µl |
| Anchored Oligo-dT 2 µg/µl | 1.0 µl |
| 20 x low-dA/NTP mix | 1.0 µl |
| a-33P dATP/a-35 dATP | 4.0 µl |
| 5 µg total RNA + H$_2$O | 6.5 µl |
| | µl |

The reaction was incubated at 65° C. for 5 min. and then cooled to 42° C. for 5 minutes. 1 µl SuperScript II enzyme was added and further incubation at 42° C. for 30 minutes was performed. Another 1 µl SuperScript II enzyme was added and incubated further at 42° C. for 30 minutes. The reaction was stopped by adding 5 µl 500 mM EDTA, and 10 µl 1 M NaOH was added and the mixture was incubated at 65° C. for 60 minutes to hydrolyse the RNA. The mixture was then cooled to room temperature and 25 µl 1 M Tris-HCL (pH 7.5) was added to neutralise the solution. Finished probes were stored on ice until cleanup.

Probe Cleanup and Preparation:

The probes were cleaned by the use of Microcon columns. 300 µl 1xTE was added to each RT-reaction and the two differently labelled samples were combined before transferring to the Microcon column and spun at 13 K until 30–50 µl solution was left. Following repeated additions and spins, a final cleaned volume of 10 µl was reached. The column was inverted into a new tube and spun in one minute at 13 K to recover the probe. In a final probe volume of 18 µl (for a cover slip size of 22×20 mm), the following was included: 1 µl 10 µg/µl COT-1 DNA, 1 µl 8 µg/µl poly A, 1 µl 4 µg/µl yeast tRNA, 1 µl 10 µg/µl BSA, 1 µl 50×Denhardt's solution, 3.1 µl 20×SSC (final concentration 3.5×SSC), and 0.5 µl 10% SDS (final concentration 0.3%). The probe was then heated in boiling water for 2 minutes before spinning at 13 K for 10 minutes.

EXAMPLE 1

Figure 4:
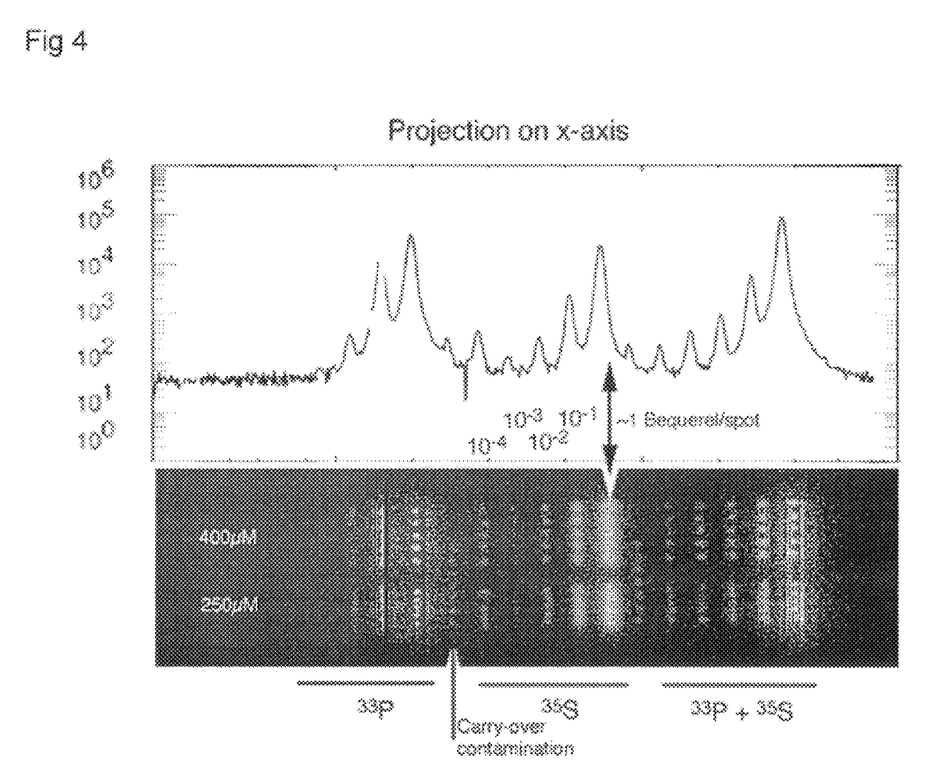
FIG. 4 shows the x-axis projection of the determination of salmon sperm labelled with $^{33}P$ and $^{35}S$, both separately and in combination.

To demonstrate the feasibility of the method and apparatus according to the invention, a model experiment with the two isotopes $^{33}P$ and $^{35}S$ diluted in salmon sperm DNA and spotted onto a glass slide to give an approximate radiation of 1 Becquerel per spot undiluted were performed. In addition a dilute series was made to dilute the 5 logs in order to demonstrate the dynamic range of the method and apparatus according to the invention. This was performed separately for each of the two isotopes, and for a combination of the isotopes. Two spot grids were employed with a centre distance of 250 µm and 400 µm. The result for all three experiments are given in FIG. 4, both as a fluorophore plot and in the form of the recorded energy spectrum as a projection of the signal onto the x-axis in order to show the quantitative relationship with dilution.

EXAMPLE 2

Figure 5:
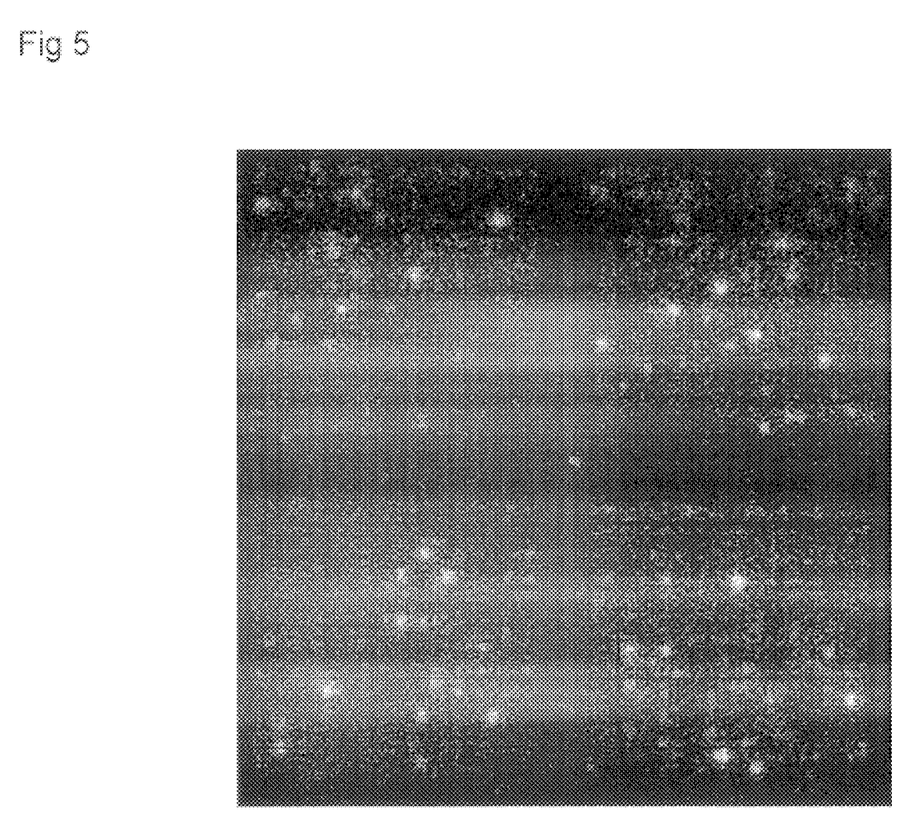
FIG. 5 shows a virtual fluorophore plot of a simultaneous determination of $^{33}P$ and $^{35}S$ labelled RNA-lines from OHS osteosarcoma and MCF-7 breast cancer cells, respectively.

In order to verify the applicability of the method and apparatus according to the invention for microarray applications, an experiment using two cell line RNAs in reduced amounts were performed. Otherwise standard microarray procedures were employed. By using RNA from two different cell lines, OHS osteosarcoma cell line and MCF-7 breast cancer cell line, a demonstration of a successful separation of the nuclides are performed, and given as a fluorophore plot in form of an overlay pseudo-colour image of the two isotopes in FIG. 5. The figure demonstrates clearly that the method and apparatus according to the invention achieves the dynamic variation of signals that may be expected from similar experiments using fluorophores, but with significantly lower starting RNA-material.

As mentioned, radioactively labelled biological substances are easily incorporated into living cells as opposed to most fluorescent substances. This may be done by adding medium substituents, such as nucleotides, amino acids, or other components where radioactive isotopes have previously been incorporated. This possibility allows for a range of new applications, in which two are described here:

EXAMPLE 3

The amount of any protein in a cell is partly regulated by the stability of it's corresponding RNA. This is generally considered to be related to the size of the poly-A tail, and partly other sequence-specific factors. To date, examination of individual mRNA species have been the method of choice. By the incorporation of two radioactive labels, it becomes possible to monitor all mRNA species in a population by comparison with a standard. This permits a genome wide scanning of RNA half life, when combined with DNA microarrays.

Instead of using cDNA with radioactivity in a cell free system enzymatically, a35S-UTP and a33P-UTP are added to the culture medium of parallel cell cultures in appropriate concentrations at time 0. Then the cells are allowed to grow until time 1, when the radioactive nucleotides are sufficiently incorporated to allow detection of RNA produced in the cells from time 0. At time 1, one parallel is treated chemically to block RNA synthesis. At time 2, both cultures are harvested, RNA is isolated, and equal amounts of RNA from both cultures are mixed. This mixture is then treated as the combined probe of cDNA in example 1 and hybridised to the microarray.

Finally the signals are recorded and analysed to find the contribution from each nucleotide in order to find the ratios. This data reflects the relative half-life of all RNA species that are detectable in the cell line. This novel procedure allows for genome wide monitoring of the important cellular regulatory function of RNA half-life in conjunction with the traditional information obtained from microarray analysis in the standard format.

EXAMPLE 4

In the emerging field of proteomics, similar methods to the one given in example 3 may be applied when using amino acid tags. For instance, the monitoring of various protein degrees of phosphorylation, a major regulatory phenomenon of all cells, may be performed by incorporating radioactivity labelled tags that are added to the medium. By printing antibody arrays, the incorporation of phosphor tags in a number of different proteins may be monitored simultaneously.

Although the invention has been described as a case of examples of comparison tests of two DNA/RNA-substances tagged with a distinctive S-emitting radionuclide each, it should be emphasised that the method and apparatus according to the invention is a general approach for determining the amounts of radioactivity tagged biological molecules that are adsorbed onto a biological microarray. This applies for all types of radioactivity including $\alpha$, $\beta$, $\gamma$, and positron radiation and all radioactive nuclides, especially those that may be incorporated into the target molecules such that the radioactivity is tuned to the order of 1–100 Becquerel from each spot of the microarray. Also, even though the method is especially suited for the case of radioactivity with overlapping energy spectra ($\beta$-emitters), one should be aware of that the statistic treatment of the registered radioactive events in the method gives advantages for monoenergetic radiation as well, especially when one applies radionuclides which emit radiation with small energy differences. These advantages include excellent filtration/separation of background noise (secondary radiation etc.) and a very high sensitivity. The method and apparatus is also designed for being applied on any number of different radioactive nuclides ranging from 1 and up. There are no theoretical limit to this number, but a practical limit is less than approx. 20, preferably less than approx. 10, and even ore preferably less than 5 different radioactive nuclides.

What is claimed is:

1. A method for simultaneous quantification of the amounts of one or more radioactive nuclides within arbitrary regions on a probe surface comprising depositing, adsorbing or fixing one or more radioactive nuclides on a probe surface; and detecting the radioactive nuclides which serve as markers on compounds that have been incorporated into target tissue sections, target chemical compounds or biological molecules that have been deposited, adsorbed or fixed to chemical or biological probe substances on said probe surface.

2. The method of claim 1 wherein both the position and energy histogram of the emitted particles or photons from each region of said probe surface are registered and accumulated as an energy band image and that the information from each image element or region of said energy band image is used to determine the amount or activity of each radioactive nuclide present on said image element or region.

3. The method of claim 2 wherein both emitted particles and photons from each region of said probe are registered and accumulated.

4. The method of claim 2 wherein said energy band image is stored as vectors of k energy bins for each image element over the entire probe surface.

5. The method of claim 4 wherein a linear combination of the pre-recorded energy spectra for every radioactive marker, wherein the unknown coefficients are the contributions from each of the radioactive nuclides, are fitted to the data from an image element or a region of the energy band image, which is the measured composite energy histogram or vector, using the least squares method, thereby providing the total number of events originating from each of the radioactive nuclides.

6. The method of claim 4 wherein the measured energy spectrum for every radioactive marker is employed to find the most probable number of hits from each radioactive marker in each energy bin which would give the registered energy histogram or vector, using the maximum likelihood method, thereby providing the total number of events originating from each of the radioactive nuclides.

7. The method of claim 2 wherein the probe regions have diameters of less than 200 micrometers.

8. The method of claim 2 wherein the probe regions have diameters of more than 300 micrometers.

9. The method of claim 1 wherein said radioactive nuclides emit either alpha, beta, gamma or positron particles or photons or both, and are incorporated into target molecules such that the radioactivity is tuned to the order of 1–100 Bq from each probe region on the probe surface.

10. The method of claim 9 wherein the beta-emitting radioactive nuclides include $33_P$ and $35_S$.

11. The method of claim 10 wherein 35S-UTP and 33P-UTP are both added to cell culture media of parallel cell cultures in appropriate concentrations at time 0; allowing the cells to grow until a time 1, when the radioactive nuclides are sufficiently incorporated to allow detection of RNA produced in the cells from time 0; treating one parallel culture at time 1 to block RNA synthesis; harvesting both cultures at time 2 and isolating equal amounts of RNA from each harvested culture; mixing the isolated RNA from each harvested culture; and treating the mixture as a combined probe of cDNA which is hybridized to a biological microarray, from which the total quantities of both radioactive markers is then determined.

12. The method of claim 11 wherein radiolabelled amino acid tags are incorporated into the cell culture medium and then adsorbed onto biological microarrays containing structured sets of antibodies for simultaneous monitoring of the degrees of phosphorylation of various sets of proteins.

* * * * *